(12) United States Patent
Koh

(10) Patent No.: US 7,988,634 B1
(45) Date of Patent: Aug. 2, 2011

(54) ADAPTIVE CANCELLATION OF A SIGNAL COMPONENT

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 212 days.

(21) Appl. No.: 11/621,944

(22) Filed: Jan. 10, 2007

(51) Int. Cl.
*A61B 5/02* (2006.01)
*A61B 5/05* (2006.01)

(52) U.S. Cl. .......................... 600/481; 600/508; 600/547

(58) Field of Classification Search .................. 600/547, 600/527
See application file for complete search history.

(56) References Cited

U.S. PATENT DOCUMENTS

| | | | |
|---|---|---|---|
| 3,452,743 A * | 7/1969 | Rieke ............................ | 600/547 |
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,309,922 A * | 5/1994 | Schechter et al. ............ | 600/534 |
| 5,466,254 A | 11/1995 | Helland | |
| 5,476,483 A | 12/1995 | Bornzin et al. | |
| 5,503,160 A * | 4/1996 | Pering et al. .................. | 600/519 |
| 6,064,910 A * | 5/2000 | Andersson et al. ............ | 607/20 |
| 6,506,153 B1 * | 1/2003 | Littek et al. .................... | 600/301 |
| 2003/0204212 A1 * | 10/2003 | Burnes et al. .................. | 607/17 |

* cited by examiner

*Primary Examiner* — Patricia Mallari

(57) ABSTRACT

A cardiac-related signal such as a cardiogenic impedance signal is derived to obtain cardiac information such as stroke volume information that may be used to evaluate cardiac performance and/or other medical conditions. In some aspects detection of the cardiogenic impedance signal involves adaptively cancelling an unwanted component of a sensed signal. For example, in some embodiments a sensed respiratory signal may be subtracted from a thoracic impedance signal to reduce a respiratory component of the thoracic impedance signal. In this way, a more accurate cardiogenic impedance signal may be derived from the resulting signal.

15 Claims, 8 Drawing Sheets

US 7,988,634 B1

ADAPTIVE CANCELLATION OF A SIGNAL COMPONENT

TECHNICAL FIELD

This application relates generally to acquisition and processing of cardiac-related signals, and to cancellation of a respiratory component of a cardiac-related signal.

BACKGROUND

A conventional method of treating a patient suffering from cardiac disease or some other cardiac disorder involves monitoring the performance of the patient's heart and applying treatment, as necessary, based on the monitored performance. For example, measurement of cardiac output provides an indication as to how effectively the heart is pumping blood. Thus, a decrease in cardiac output may indicate that the patient's condition is worsening and, consequently, that new therapy should be administered to the patient or the at the patient's current therapy should be modified.

Conventionally, cardiac output may be approximated based on analysis of other cardiac parameters. One such parameter is stroke volume—the volume of a blood ejected from a ventricular chamber upon contraction of the ventricle. Stroke volume may be estimated based on analysis of a sensed thoracic impedance signal. Here, a sensing mechanism may measure impedance across a portion of the thoracic cavity of a patient over a given time period. The time derivative of the thoracic impedance is known as cardiogenic impedance. Stroke volume information may be derived from the cardiogenic impedance. For example, stroke volume information may be derived from the maximum of the cardiogenic impedance signal and from ventricle ejection time derived from the cardiogenic impedance signal.

Typically, the thoracic impedance signal includes one or more signal components in addition to a cardiogenic component. For example, air moving into and out of the lungs may affect the measured thoracic impedance. Thus, a thoracic impedance signal may contain a respiratory component that corresponds to the breathing pattern of the patient. A thoracic impedance signal also may include signal component resulting from motion of the patient.

In practice, it may be difficult to separate a cardiac-related component (from which cardiogenic impedance is derived) from other components of the thoracic impedance signal due to the relatively similar frequency characteristics of these components. For example, the bandwidth of the cardiac-related component may be on the order of 0.8-20 Hz. The bandwidth of the respiratory component may be on the order of 0.04-2 Hz. The bandwidth of a motion-related component may be on the order of 0.1-10 Hz. Given the relative similarity of these frequency ranges, conventional linear techniques may not provide a sufficiently effective mechanism for separating the thoracic impedance signal components.

Other techniques such as cessation of breathing, ensemble averaging and adaptive digital filtering have been proposed for removing a respiratory component from a thoracic impedance signal. However, each of these techniques may have one or more drawbacks. For example, for a patient with cardiac-related problems it may not be practical or advisable to have the patient hold his or her breath every time a thoracic impedance measurement is taken.

Ensemble averaging may be used to suppress beat-to-beat variations and transients in the derived cardiogenic component signal. This process, however, tends to suppress the distinctive A/B/X notch in the cardiogenic impedance signal. This, in turn, may adversely affect derivation of the stroke volume information because accurate calculation of stroke volume may depend on accurate acquisition of the A/B/X notch information.

A high pass infinite impulse response digital filter may be used to filter out a respiratory component. Such a filter may incorporate a varying cutoff frequency to compensate for changes in the heart rate of a patient. In practice, however, such a technique may distort signals in hearth rhythm transition. For example, the filter may not have advance knowledge as to when a patient's activity level will change between exercise and resting states. As a result, improper filtering may be employed during these transitions.

SUMMARY

A summary of various aspects and/or embodiments of an apparatus constructed or a method practiced according to the invention follows. For convenience, one or more embodiments of an apparatus constructed or a method practiced according to the invention may be referred to herein simply as an "embodiment" or "embodiments."

The invention relates in some aspects to detecting cardiac-related signals such as a cardiogenic impedance signal. Such a signal may be used to obtain cardiac information such as stroke volume information that may, in turn, be used to evaluate cardiac performance and/or other medical conditions.

Some aspects relate to reducing (e.g., cancelling) a respiratory component of a cardiac-related signal such as a thoracic impedance signal. For example, in some embodiments a sensed respiratory signal is used to reduce the respiratory component of a sensed thoracic impedance signal. In this way, a more accurate cardiogenic impedance signal may be derived from the resulting thoracic impedance signal due to the reduction of the respiratory component.

In some embodiments a filtered respiratory signal is subtracted from a delayed thoracic impedance signal. Here, the filtering and the delaying may be used in an attempt to ensure that the respiratory signal that is being subtracted corresponds (e.g., in time and form) to the respiratory component of the thoracic impedance signal.

Various conditions may be sensed to obtain a respiratory signal. For example, some embodiments may sense one or more of oxygen saturation, acceleration, blood pressure, phrenic neural activity or some other condition to obtain the respiratory signal. To this end, some embodiments may employ one or more of an SVO2 sensor, a photoplethysmography sensor, an accelerometer, a blood pressure sensor, a phrenic neural sensor or some other type of sensing apparatus.

BRIEF DESCRIPTION OF THE DRAWINGS

These and other features, aspects and advantages of the invention will be more fully understood when considered with respect to the following detailed description, appended claims and accompanying drawings, wherein:

Figure 1:
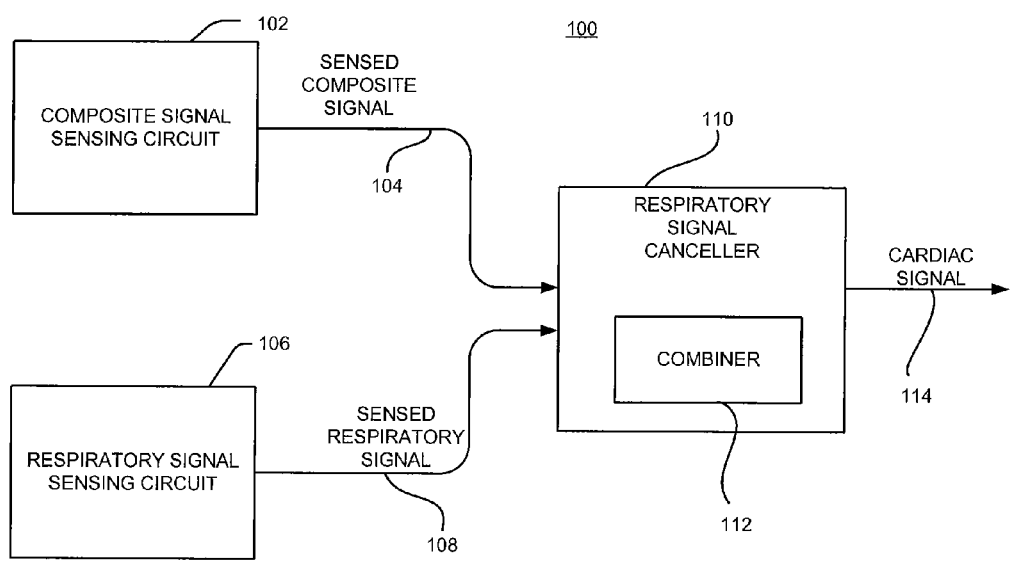
FIG. 1 is a simplified block diagram of an embodiment of an apparatus adapted to derive a cardiac-related signal from sensed signals.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s).

Figure 2:
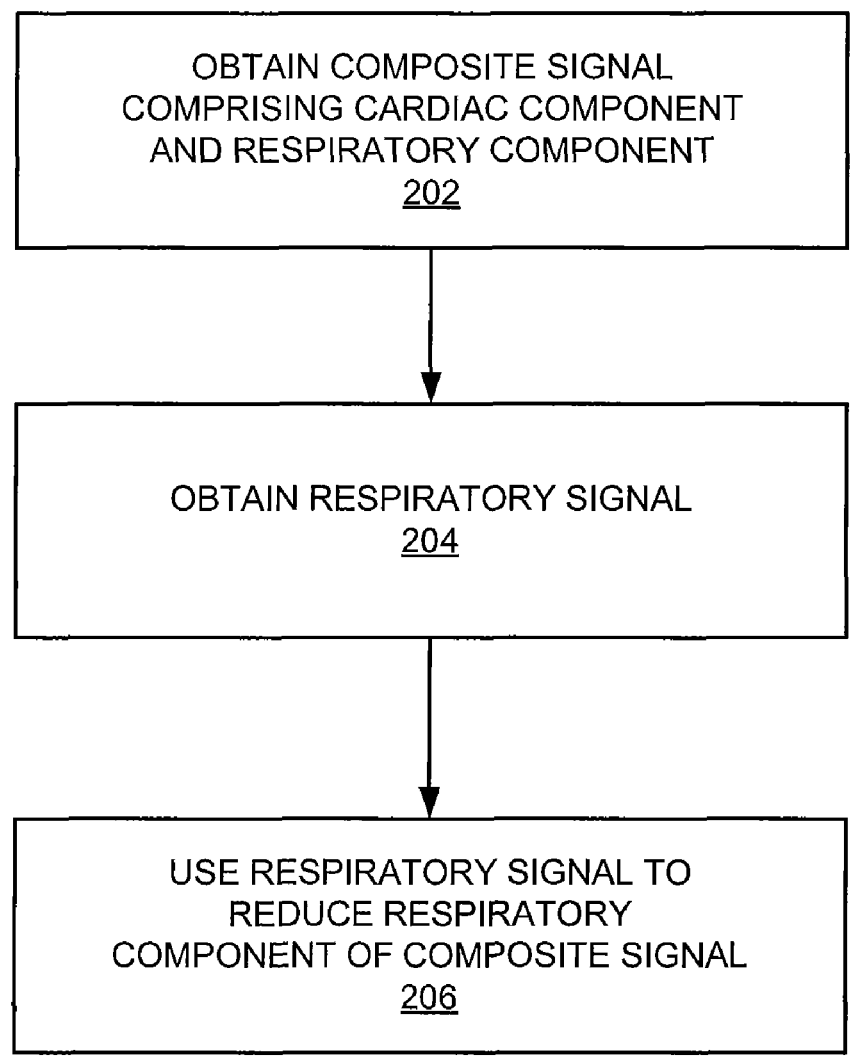
FIG. 2 is a flow chart of an embodiment of operations that may be performed to derive a cardiac-related signal from sensed signals.

FIGS. 1 and 2 illustrate, from a high-level perspective, an embodiment of an apparatus 100 and an embodiment of operations, respectively, employing respiratory signal cancellation to generate a cardiac-related signal based on signals sensed from a patient. For convenience, the operations of FIG. 2 (and any other operations herein) may be described as being performed by specific components. It should be appreciated, however, that these operations may be performed in conjunction with or by other components.

As represented by block 202 of FIG. 2, a sensing circuit 102 is adapted to obtain a composite signal 104 from the patient. In some embodiments the signal 104 may comprise a thoracic impedance signal that comprises a cardiogenic component and a respiratory component (e.g., an unwanted artifact). As will be discussed in more detail below, the sensing circuit 102 may include one or more components that are implanted in the patient.

As represented by block 204, a sensing circuit 106 is adapted to obtain a respiratory signal 108 from the patient. As will discussed in more detail below, the sensing circuit 106 also may include one or more components that are implanted in the patient.

As represented by block 206, a respiratory signal canceller 110 is adapted to use the respiratory signal 108 to reduce the respiratory component of the composite signal 104. For example, the respiratory signal canceller 110 may comprise a combiner 112 (e.g., a signal summer) adapted to subtract the respiratory signal 108 from the composite signal 104. The respiratory signal canceller 110 may thereby generate a signal 114 substantially comprising the cardiogenic component.

Generally stated, this adaptive cancellation technique involves acquiring or estimating a replica of an unwanted signal component (e.g., the respiratory component) and adding the replica to the composite signal such that the replica is 180 degree out of phase with the unwanted signal component. Here, provisions (e.g., filtering, gain control, etc.) may be employed in an attempt to effectively match the characteristics of the replica with the unwanted signal. The adaptive cancellation technique may be used to cancel one or more unwanted components of a signal (e.g., to reject different types of signal components). Furthermore, this technique may be used to reject a signal component with varying and/or unpredictable characteristics. For example, this technique may be used to reduce a respiratory component of an impedance signal, where the patient's respiration pattern may be unknown and frequently changing. Advantageously, effective cancellation may be achieved without having to control the patient's respiration (e.g., to conform to a known pattern).

Figure 3:
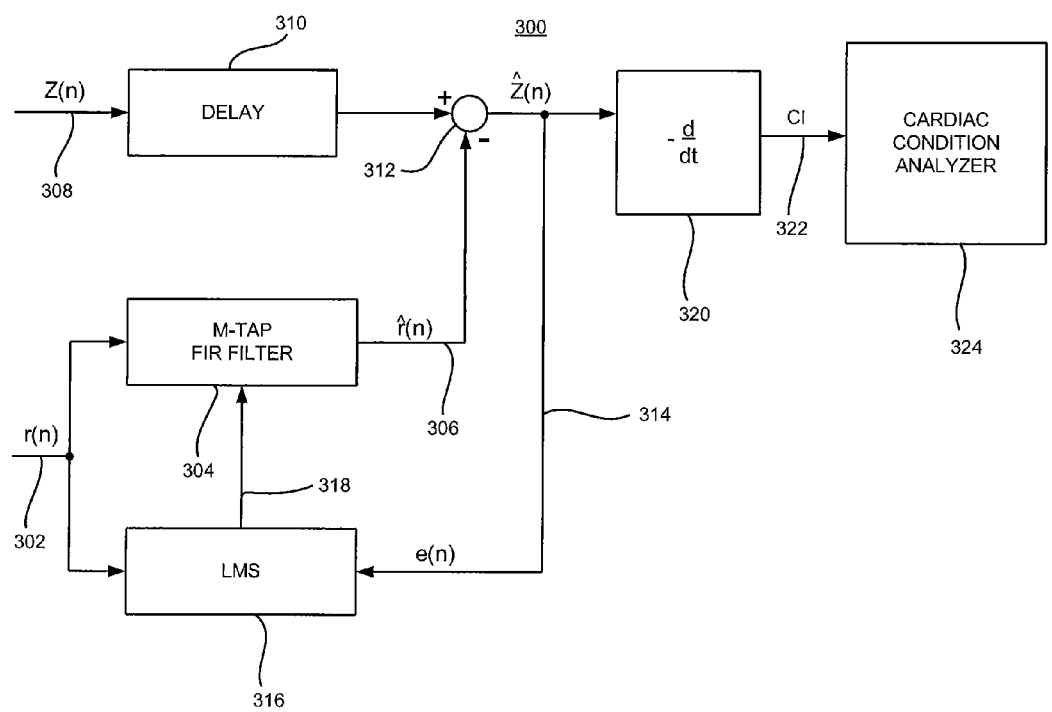
FIG. 3 is a simplified block diagram of an embodiment of an apparatus adapted to cancel a respiratory component of a thoracic impedance signal.
Figure 4:
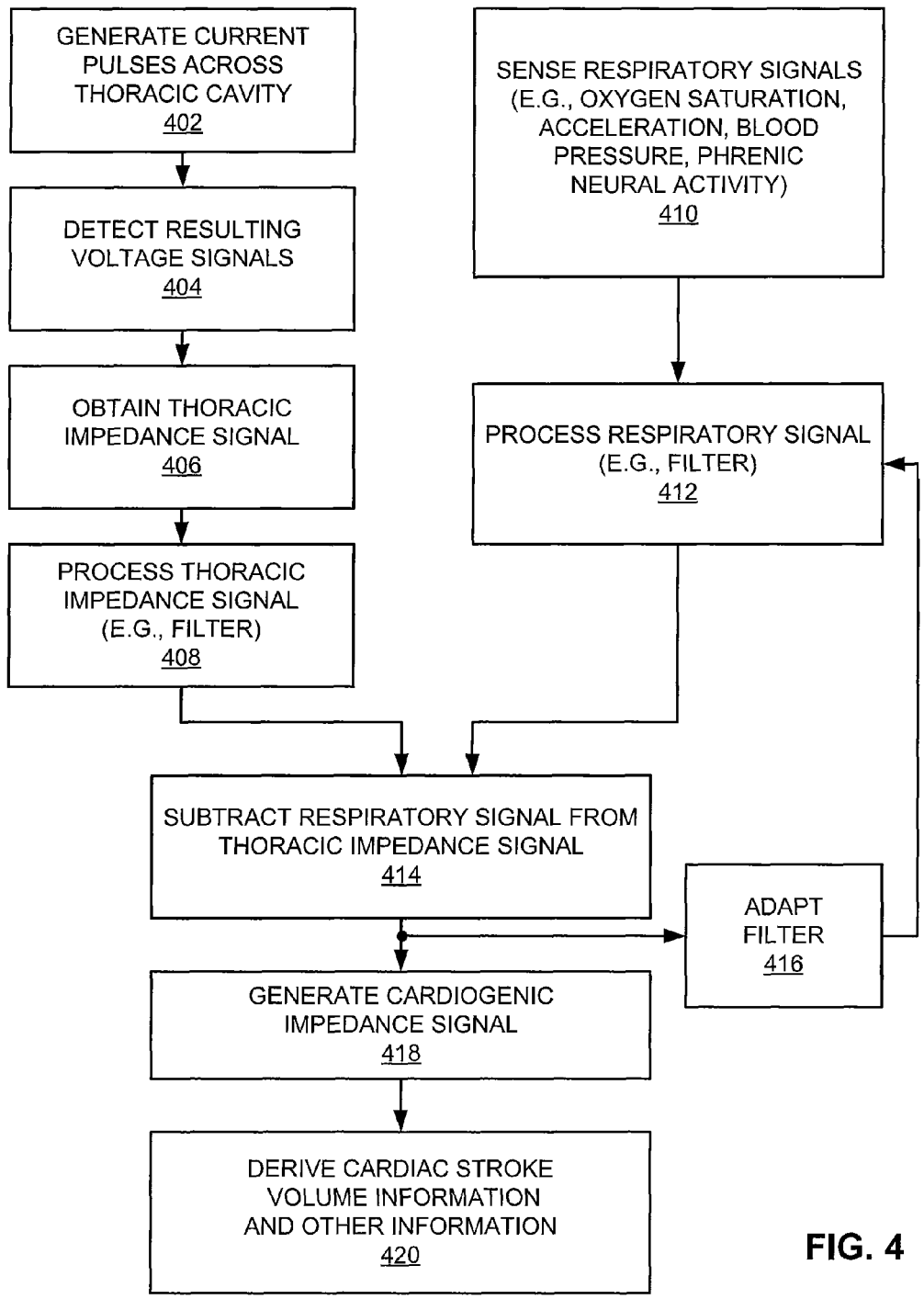
FIG. 4 is a flow chart of an embodiment of operations that may be performed in conjunction with cancellation of a respiratory component of a thoracic impedance signal.

Referring now to FIGS. 3 and 4, selected details of an implementation that derives a cardiogenic signal by measuring transthoracic impedance and subtracting a sensed respiratory signal from the resulting thoracic impedance signal will be treated in some detail. It should be appreciated, however, that the specific components and operations described below are provided for illustrative purposes and that the teachings herein may be applicable to other components and operations.

Figure 7:
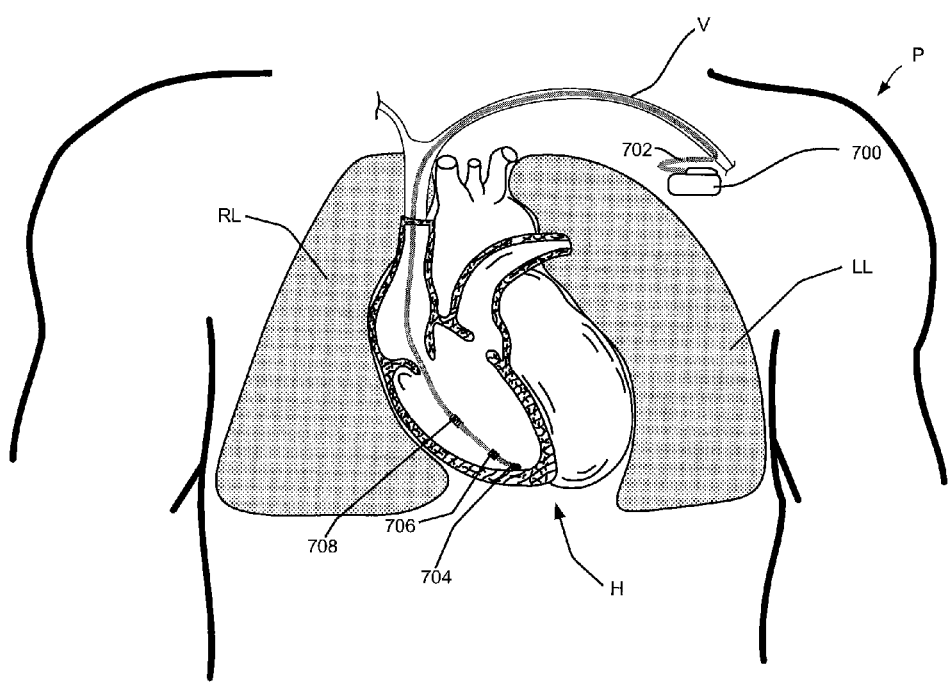
FIG. 7 is a simplified cutaway view of an embodiment of a cardiac device implanted in a patient and in electrical communication with at least one lead implanted in a patient's heart for sensing conditions in the patient and delivering therapy to the patient.

Blocks 402-408 of FIG. 4 relate to operations that may be performed to obtain a thoracic impedance signal. In some embodiments this may be accomplished through the use of one or more implanted leads as discussed herein or any other suitable lead or mechanism. A brief explanation will be provided in conjunction with the example of a device 700 and an associated lead 702 that are implanted in a patient P as shown in FIG. 7. Here, as represented by block 402 of FIG. 4, impedance may be measured by sending a signal (e.g., a series of short current pulses) between one or more of the electrodes 704 and 706 on the lead 702 and an electrode provided by the case of the device 700 (the "case" electrode). Then, as represented by block 404, a resulting signal (e.g., corresponding voltage pulses) may be sensed using the same or different electrodes. With each heartbeat, the resulting action of the heart and blood will cause a corresponding, repetitive change in the measured impedance. In this way, a cardiac signal component is effectively modulated on the measured impedance.

Moreover, FIG. 7 also illustrates that the impedance path for this signal may include at least a portion of the left lung ("LL") and/or at least a portion of the right lung ("RL"). Consequently, as air moves into and out of the lungs RL and LL when the patient P breaths, the measured impedance will change thereby causing a respiratory signal to be effectively modulated on the measured impedance.

As represented by block 406, by repeatedly generating the current pulses and detecting the resulting voltage signals, a series of measured impedance values may be obtained. This time series of values may thus provide a thoracic impedance signal that comprises the above cardiac-related and respiratory-related components.

Figure 5:
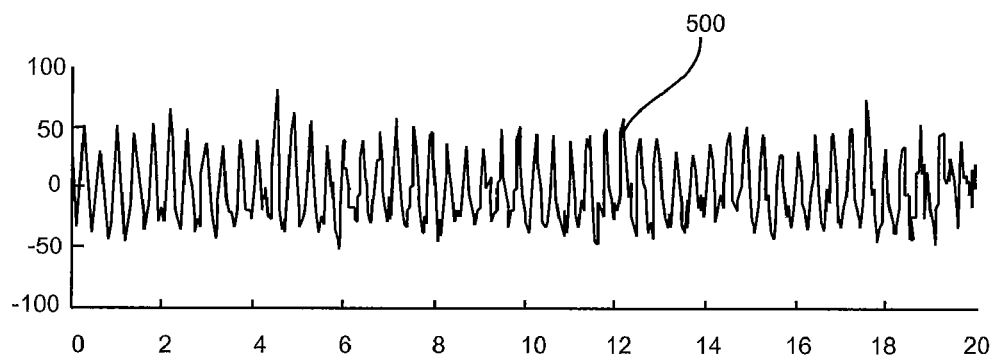
FIG. 5 is a simplified diagram illustrating an impedance signal having a cardiogenic component and a respiratory component.

FIG. 5 illustrates an example of a sensed impedance signal 500. In this example, raw impedance signal samples have been filtered to obtain a relatively continuous impedance signal 500 (block 408). The repetitive pulses of the signal 500 correspond to the heart beat of the patient. Thus, these pulses illustrate a cardiogenic component of the impedance signal.

In addition, the respiratory component of the signal 500 is evident from the variation in the maximums or minimums of the signal 500. Here it may be seen that the signal 500 is, in effect, amplitude modulated by a slower, relatively sinusoidal signal.

Blocks 410 and 412 of FIG. 4 relate to operations that may be performed to obtain a respiratory signal. As represented by block 410, a respiratory signal may be obtained by, for example, sensing one or more physiologic conditions that are affected by respiration. Several examples include the oxygen saturation of the patient's blood, acceleration in or near the thoracic cavity, the blood pressure of the patient and phrenic neural activity. It should be appreciated that these are but a few examples of conditions or characteristics that may be sensed or monitored to obtain respiration information.

Various components may be employed to sense the above conditions or characteristics. For example, an SVO2 sensor may be used to sense oxygen saturation. A photoplethysmography ("PPT") sensor also may be used to sense oxygen saturation. These sensors may be implanted in the patient in a manner that enables the sensor to monitor oxygen saturation in the patient's cardiovascular system. In some embodiments such a sensor may monitor oxygen levels in the pulmonary system before the lungs. For example, a sensor may be located in the right ventricle, the inferior vena cava ("IVC") or some other suitable location. Typically, a respiratory signal sensed via oxygen saturation levels may be relatively sinusoidal in nature.

An accelerometer may be used to sense acceleration. In embodiments that incorporate an implantable cardiac device, an accelerometer may be located in the implantable cardiac device. Alternatively, an accelerometer may be implanted at some other suitable location within the patient. A respiratory signal sensed via acceleration also may be relatively sinusoidal in nature.

A blood pressure sensor may be used to measure blood pressure. In some embodiments a blood pressure sensor may be implanted in a cardiac chamber. For example, a blood pressure sensor may be incorporated into a lead implanted into the left atrium, the right ventricle, or some other suitable chamber or vessel. A respiratory signal sensed via blood pressure levels may be relatively sinusoidal in nature.

A sensor mechanism such as an electrode (e.g., in the form of a coil) may be used to measure phrenic neural activity. Such an electrode may, for example, be implanted such that it is wrapped around or is positioned adjacent to the phrenic nerve. A respiratory signal sensed via phrenic neural activity is generally not sinusoidal in nature. Rather, the signal is, in general, active when the patient inhales and not active when the patient exhales; the latter being essentially a recoil action. Accordingly, a signal sensed via phrenic neural activity may be processed (e.g., filtered) to provide a respiratory signal that more closely approximates the respiratory component of the thoracic impedance signal.

As represented by block 412 of FIG. 4, some form of processing may thus be applied to a sensed respiratory signal. In particular, any of the above signals may be filtered so that the signal more closely approximates the respiratory component of the thoracic impedance signal. Referring to FIG. 3, a sensed respiratory signal r(n) 302 is provided to a filter 304 to generate a filtered respiratory signal r̂(n) 306. In the example of FIG. 3, the filter 304 is a finite impulse response ("FIR") filter that incorporates "M" taps. It should be appreciated that other types of filters may be employed to generate a filtered respiratory signal r̂(n) 306.

To compensate for the delay imparted on the respiratory signal r(n) by the filter 304, a thoracic impedance signal Z(n) 308 (including cardiogenic and respiratory components) generated at block 408 may be coupled to a delay element 310. For example, the delay of the delay element 310 may be set equal to the delay of the filter 304. In addition, the delay may be specified to take into account delays resulting from sensing of the input signals or any other delay that may affect the relative timing of the respiratory component and the respiratory signal. In this way, the thoracic impedance signal Z(n) 308 and the filtered respiratory signal r̂(n) 306 may be aligned in time to improve the cancellation of the respiratory component in the thoracic impedance signal Z(n) 308.

In practice, the functions of one or more of the components of FIG. 3 may be implemented in either the analog domain or the digital domain. FIG. 3 illustrates an embodiment implemented in the digital domain wherein the input signals r(n) 302 and Z(n) 308 are digital signals. Accordingly, in this case analog-to-digital processing may be employed to provide the appropriate digital input signals. It should be appreciated, however, that in other embodiments analog-to-digital processing may be employed at a later stage in the operations of FIG. 3.

Blocks 414-420 of FIG. 4 relate to processing operations that may be performed on the above signals. As represented by block 414, a summer 312 subtracts the filtered respiratory signal r̂(n) from the delayed thoracic impedance signal. Ideally, the resulting thoracic impedance signal Ẑ(n) would no longer contain a respiratory component. In practice, however, the respiratory signal r(n) may not exactly match the respiratory component of the thoracic impedance signal Z(n). Accordingly, the summer 312 may merely reduce, rather than completely eliminate, the respiratory component of the thoracic impedance signal Z(n).

Advantageously, through the use of this cancellation technique the resulting thoracic impedance signal Ẑ(n) may not be as attenuated as it may otherwise be using other techniques. For example, a technique that only employs filtering to remove an undesired component of a signal also would likely attenuate a desired component of the signal in the event the undesired and desired components have frequency ranges that overlap.

In practice, the thoracic impedance signal Z(n) 308 may comprise a motion-related signal component. Here, the patient's movement may cause some variation in the sensed impedance signal. However, the respiratory signal r(n) 302 also may comprise a motion-related signal component. Consequently, the operation of the summer 312 may reduce the motion-related component from the thoracic impedance signal Z(n) 308. In some embodiments the filtering and/or delaying of the thoracic impedance signal Z(n) 308 and/or the respiratory signal r(n) 302 may be adapted in an attempt to improve this rejection of the motion-related component.

As represented by block 416, in some embodiments the filter 304 may comprise an adaptive filter. In this case, the characteristics of the filter 304 may be continually adapted in an attempt to provide a filtered respiratory signal r(n) 306 that most closely matches the respiratory component of the impedance signal Z(n) 308. In the example of FIG. 3, the output of the summer 312 provides an error signal e(n) 314 for a least mean square ("LMS") component 316. The LMS component 316 provides a coefficient signal 318 to the filter 304 based on the error signal e(n) 314 and the respiratory signal r(n) 302. Here, the LMS component 316 may adjust the coefficient signal 318 to reduce a mean square error based on the error signal e(n) 314. Equations 1-3 that follow provide an example of the operation of the circuit of FIG. 3. Here, $n_d$ relates to the delay of delay element 310, $w_n(k)$ relates to the coefficient signal 318 that is adjusted using Equation 3, and p is a loop weighting factor.

$$\hat{r}(n) = \sum_{k=0}^{M-1} r(n-k)w_n(k) \qquad \text{EQUATION 1}$$

$$\hat{Z}(n) = Z(n-n_d) - \hat{r}(n) \qquad \text{EQUATION 2}$$

$$w_{n+1}(k) = w_n(k) + 2\mu\hat{Z}(n)r(n-k) \qquad \text{EQUATION 3}$$

The FIR filter 304 and the LMS component 316 described above are provided as examples of suitable components. It should be appreciated that other filtering mechanisms and adaptation techniques may be employed to provide a signal for removing an unwanted component of a signal such as the impedance signal Z(n) 308.

As represented by block 418, a component 320 may derive a cardiogenic impedance signal ("CI") 322 from the signal $\hat{Z}(n)$ output by the summer 312. As discussed above, this process may involve a time derivative function (e.g., −dZ/dT) or some other suitable function.

Figure 6:
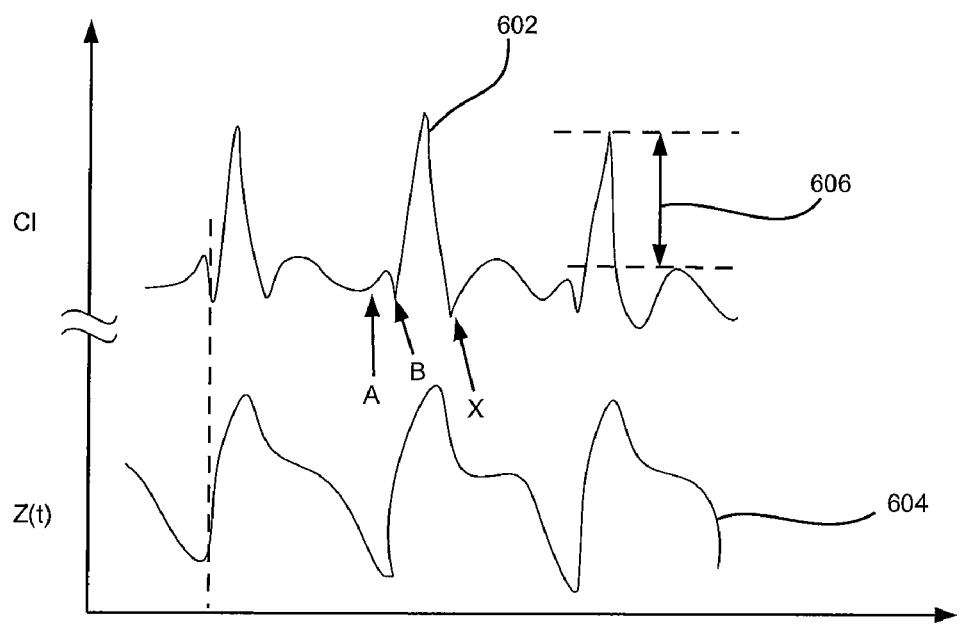
FIG. 6 is a simplified diagram illustrating an example of an impedance signal and a cardiogenic impedance signal derived from the impedance signal.

FIG. 6 illustrates an example of several cycles of a cardiogenic impedance ("CI") signal 602 and a thoracic impedance signal 604 from which the cardiogenic impedance signal 602 may be derived. Similar to the example of FIG. 5, the thoracic impedance signal 604 has been filtered to provide a relatively smooth signal. FIG. 6 also illustrates that the resulting cardiogenic signal 602 may advantageously provide a well defined A/B/X notch that may not be as attenuated as it may otherwise be using other techniques. In addition, an arrow 606 in FIG. 6 illustrates the maximum cardiogenic impedance parameter.

Accordingly, as represented by block 420 in FIG. 4, a cardiac condition analyzer component or some other suitable component 324 may process the cardiogenic impedance signal 322 to obtain parameters that may be used to estimate stroke volume or some other indication of cardiac activity. In particular, the component 324 may derive ventricle (e.g., left ventricle) ejection time and maximum cardiogenic impedance information from the cardiogenic impedance signal 322 and use this information to derive stroke volume information. The component 324 may then use the stroke volume information to determine cardiac output or some other cardiac function.

In addition, a decrease in dZ/dT over time may indicate that the contractility of the heart is decreasing—a potential indication of progression of heart failure. Accordingly, this condition may be tracked over time by repeatedly monitoring the cardiogenic impedance signal.

Based on these and/or other indications, various steps may be taken to provide appropriate treatment for the patient, if necessary. For example, appropriate indications may be made, patient therapy may be called for, applied or modified, or warnings may be sent to the patient or the patient's doctor.

Exemplary Cardiac Device

With the above in mind, additional details of processing cardiac-related and respiratory signals will be discussed in conjunction with a specific example where at least a portion of the processing is performed by an implantable cardiac device (e.g., a stimulation device such as an implantable cardioverter defibrillator, a pacemaker, etc.). It should be appreciated that this example is provided for explanatory purposes and that such signal processing may be implemented using any suitable implantable medical device (e.g., a monitoring device) or some other suitable device, including a device that is not necessarily implantable.

FIG. 7 illustrates an exemplary implantable cardiac device 700 in electrical communication with a heart H of a patient P by way of an implantable right ventricular lead 702, suitable for sensing cardiac activity and delivering stimulation (e.g., pacing and shocking) therapy. In this example, the lead 702 includes a right ventricular tip electrode 704, a right ventricular ring electrode 706 and a right ventricular (RV) coil electrode 708. In some embodiments the device 700 also may be in electrical communication with the patient's heart H by way of a superior vena cava (SVC) coil electrode (not shown) on the lead 702.

In the example of FIG. 7, the device 700 is implanted subcutaneously in the pectoral region of the patient P and the right ventricular lead 702 is inserted into a vein V then routed into the heart H. In a typical implementation the lead 702 is configured and implanted to place the right ventricular tip electrode 704 in the right ventricular apex so that the RV coil electrode 708 will be positioned in the right ventricle and an SVC coil electrode will be positioned in the superior vena cava. Accordingly, the right ventricular lead 702 is capable of sensing or receiving cardiac signals, and delivering stimulation in the form of pacing and shock therapy to the heart.

In practice, the device 700 may be coupled to several leads (not shown) to provide multi-chamber sensing and stimulation. For example, to sense right atrial cardiac signals and to provide right atrial chamber stimulation therapy, the device 700 may be coupled to an implantable right atrial lead (not shown) having, for example, an atrial tip electrode that is typically implanted in the patient's right atrial appendage or septum, and an atrial ring electrode.

To sense left atrial and ventricular cardiac signals and to provide left chamber pacing therapy, the device 700 may be coupled to a coronary sinus lead (not shown) designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

An exemplary coronary sinus lead may be designed to receive atrial and ventricular cardiac signals and to deliver left ventricular pacing therapy using, for example, a left ventricular tip electrode and, optionally, a left ventricular ring electrode; provide left atrial pacing therapy using, for example, a left atrial ring electrode; and provide shocking therapy using, for example, a left atrial coil electrode. For a more detailed description of a coronary sinus lead, the reader is directed to U.S. Pat. No. 5,466,254, "Coronary Sinus Lead with Atrial Sensing Capability" (Helland), which is incorporated herein by reference.

It should be appreciated that the device 700 may be coupled to various types of leads other than those specifically shown or described herein. In addition, a lead may be implanted using various techniques and at various locations. For example, a lead may be positioned in, near or remote from the heart.

A lead connected to the device 700 may include components other than those shown in FIG. 7. For example, a lead may include other types of electrodes, sensors (e.g., a physiologic sensor) or devices that serve to otherwise interact with a patient or the surroundings. In particular, the device 700, in conjunction with one or more sensors incorporated into one or more implantable leads, may sense a respiratory signal. In practice, the characteristics of the sensed signal may depend on the position of a sensor. Accordingly, a specific location selected for placement of a sensor may depend on the requirements of a given application. The resulting sensed respiratory signal may then be processed by the device 700 in a manner as discussed herein.

Furthermore, the device 700, in conjunction with one or more implantable cardiac leads (e.g., the lead 702 or any other lead discussed herein), may sense cardiac electrical signals to generate thoracic impedance signals. As mentioned above, pulse signals may be generated using a pair of electrodes (e.g., the electrode 702 and the "case" electrode) such that a resulting signal may be sensed using the same electrodes or different electrodes. In practice, the characteristics of the sensed signal may depend on the positions of the electrodes. Accordingly, specific locations selected for placement of the electrodes may depend on the requirements of a given application. In any event, the sensed signal may be processed by the device 700 in a manner as discussed herein to, for example, derive a thoracic impedance signal and other signals and/or information.

Figure 8:
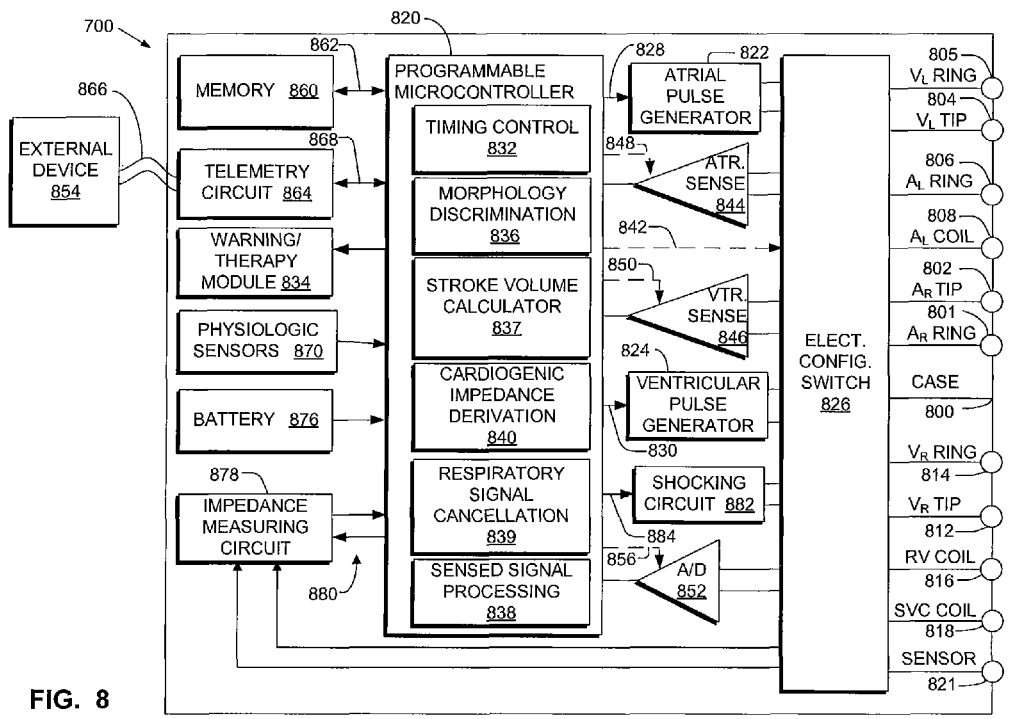
FIG. 8 is a simplified functional block diagram of an embodiment of implantable cardiac device, illustrating basic elements that may be configured to sense conditions in the patient and deliver therapy to the patient.

FIG. 8 is a simplified block diagram depicting various components of an exemplary cardiac device 700. In some embodiments the primary function of the device 700 is to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described herein may be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 800 for device 700 is often referred to as the "can", "case" or "case electrode", and may be programmably selected to act as the return electrode for all "unipolar" modes. Housing 800 may further be used as a return electrode alone or in combination with one or more of the coil electrodes (e.g., electrode 708) for shocking purposes. Housing 800 further includes a connector (not shown) having a plurality of terminals 801, 802, 804, 805, 806, 808, 812, 814, 816 and 818 (shown schematically and, for convenience, the names of the electrodes to which they may be connected are shown next to the terminals). The connector may be configured to include various other terminals depending on the requirements of a given application. For example, in some embodiments the connector may include one or more terminals 821 that connect to one or more external sensors (not shown).

To achieve right atrial sensing and pacing, the connector includes, for example, a right atrial tip terminal (AR TIP) 802 adapted for connection to a right atrial tip electrode. A right atrial ring terminal (AR RING) 801 may also be included and adapted for connection to a right atrial ring electrode. To achieve left chamber sensing, pacing, and shocking, the connector includes, for example, a left ventricular tip terminal (VL TIP) 804, a left ventricular ring terminal (VL RING) 805, a left atrial ring terminal (AL RING) 806, and a left atrial shocking terminal (AL COIL) 808, which are adapted for connection to a left ventricular tip electrode, a left ventricular ring electrode, a left atrial ring electrode, and a left atrial coil electrode, respectively.

To support right chamber sensing, pacing, and shocking, the connector further includes a right ventricular tip terminal (VR TIP) 812, a right ventricular ring terminal (VR RING) 814, a right ventricular shocking terminal (RV COIL) 816, and a superior vena cava shocking terminal (SVC COIL) 818, which are adapted for connection to the right ventricular tip electrode 704, the right ventricular ring electrode 706, the RV coil electrode 708, and an SVC coil electrode, respectively.

At the core of the device 700 is a programmable microcontroller 820 that controls the various modes of stimulation therapy. As is well known in the art, microcontroller 820 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 820 includes the ability to process or monitor input signals (data or information) as controlled by a program code stored in a designated block of memory. The type of microcontroller is not critical to the described implementations. Rather, any suitable microcontroller (e.g., a signal processor) or other processing component(s) may be used for carrying out the functions described herein. The use of microprocessor-based control circuits for performing timing and data analysis functions are well known in the art.

Representative types of control circuitry that may be used in connection with the described embodiments may include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals that may be used within the device 700 and their inter-relationship, see U.S. Pat. No. 4,788,980 (Mann et al.), also incorporated herein by reference.

FIG. 8 also shows an atrial pulse generator 822 and a ventricular pulse generator 824 that generate pacing stimulation pulses for delivery by a right atrial lead, a coronary sinus lead, and/or the right ventricular lead 702 via an electrode configuration switch 826. It is understood that in order to provide stimulation therapy in each of the four chambers of the heart, the atrial and ventricular pulse generators 822 and 824 may include dedicated, independent pulse generators, multiplexed pulse generators, or shared pulse generators. The pulse generators 822 and 824 are controlled by the microcontroller 820 via appropriate control signals 828 and 830, respectively, to trigger or inhibit the stimulation pulses.

Microcontroller 820 further includes timing control circuitry 832 (e.g., implementing one or more timers) to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, or other time periods, as is known in the art.

Microcontroller 820 further includes an arrhythmia detector (not shown). The arrhythmia detector may be utilized by the device 700 for determining desirable times to administer various therapies. The arrhythmia detector may be implemented, for example, in hardware as part of the microcontroller 820 and/or as software/firmware instructions programmed into the device and executed on the microcontroller 820 during certain modes of operation.

Microcontroller 820 may include a morphology discrimination module 836, a capture detection module (not shown) and an auto sensing module (not shown). These modules are optionally used to implement various exemplary recognition algorithms and/or methods. The aforementioned components may be implemented, for example, in hardware as part of the microcontroller 820 and/or as software/firmware instructions programmed into the device and executed on the microcontroller 820 during certain modes of operation.

The electrode configuration switch 826 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 826, in response to a control signal 842 from the microcontroller 820, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 844 and ventricular sensing circuits (VTR. SENSE) 846 may also be selectively coupled to a right atrial lead, a coronary sinus lead, and the right ventricular lead 702, through the switch 826 for detecting the presence of cardiac activity in each of the four chambers of the heart. Accordingly, the atrial and ventricular sensing circuits 844 and 846 may include dedicated sense amplifiers, multiplexed amplifiers, or shared amplifiers. Switch 826 determines the "sensing polarity" of the cardiac signal by selectively closing the appropriate switches, as is also known in the art. In this way, the clinician may program the sensing polarity independent of the stimulation polarity. The sensing circuits (e.g., circuits 844 and 846) are optionally capable of obtaining information indicative of tissue capture.

Each sensing circuit 844 and 846 preferably employs one or more low power, precision amplifiers with programmable gain and/or automatic gain control, bandpass filtering, and a threshold detection circuit, as known in the art, to selectively sense the cardiac signal of interest. The automatic gain control enables the device 700 to deal effectively with the difficult problem of sensing the low amplitude signal characteristics of atrial or ventricular fibrillation.

The outputs of the atrial and ventricular sensing circuits 844 and 846 are connected to the microcontroller 820, which, in turn, is able to trigger or inhibit the atrial and ventricular pulse generators 822 and 824, respectively, in a demand fashion in response to the absence or presence of cardiac activity in the appropriate chambers of the heart. Furthermore, as described herein, the microcontroller 820 is also capable of analyzing information output from the sensing circuits 844 and 846 and/or a data acquisition system 852. This information may be used to determine or detect whether and to what degree tissue capture has occurred and to program a pulse, or pulses, in response to such determinations. The sensing circuits 844 and 846, in turn, receive control signals over signal lines 848 and 850 from the microcontroller 820 for purposes of controlling the gain, threshold, polarization charge removal circuitry (not shown), and the timing of any blocking circuitry (not shown) coupled to the inputs of the sensing circuits 844 and 846 as is known in the art.

For arrhythmia detection, the device 700 utilizes the atrial and ventricular sensing circuits 844 and 846 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector of the microcontroller 820 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 852. The data acquisition system 852 is configured (e.g., via signal line 856) to acquire analog signals, convert the raw analog signals into a digital signal, and store the digital signals for later processing and/or telemetric transmission to an external device 854. For example, the data acquisition system 852 may be coupled to a right atrial lead, a coronary sinus lead, the right ventricular lead 702 and other leads through the switch 826 to sample cardiac signals across any pair of desired electrodes.

The data acquisition system 852 also may be coupled to receive signals from other input devices. For example, the data acquisition system 852 may sample signals from leads or other components (e.g., via terminal 821, etc.) coupled to the switch 826. In addition, the data acquisition system 852 may sample signals from a physiologic sensor 870 or other components shown in FIG. 8 (connections not shown).

Typically, the data acquisition system 852 is configured (e.g., via signal line 856) to acquire intracardiac electrogram ("IEGM") signals. For example, as discussed above, one or more of the leads implanted in the heart H may sense cardiac electrical signals. These signals may thus be coupled to the data acquisition system 852 via the switch 826. The raw IEGM signal data may then be provided to the microcontroller 820 for processing.

The microcontroller 820 is further coupled to a memory 860 by a suitable data/address bus 862, wherein the programmable operating parameters used by the microcontroller 820 are stored and modified, as required, in order to customize the operation of the device 700 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 852), which data may then be used for subsequent analysis to guide the programming of the device or for other operations.

Advantageously, the operating parameters of the implantable device 700 may be non-invasively programmed into the memory 860 through a telemetry circuit 864 in telemetric communication via communication link 866 with the external device 854, such as a programmer, transtelephonic transceiver, a diagnostic system analyzer or some other device. The microcontroller 820 activates the telemetry circuit 864 with a control signal (e.g., via bus 868). The telemetry circuit 864 advantageously allows intracardiac electrograms and status information relating to the operation of the device 700 (as contained in the microcontroller 820 or memory 860) to be sent to the external device 854 through an established communication link 866.

The device 700 can further include one or more physiologic sensors 870. In some embodiments the device 700 may include a "rate-responsive" sensor that may provide, for example, information to aid in adjustment of pacing stimulation rate according to the exercise state of the patient. One or more physiologic sensors 870 (e.g., a pressure sensor) may further be used to detect changes in cardiac output, changes in the physiological condition of the heart, or diurnal changes in activity (e.g., detecting sleep and wake states). Accordingly, the microcontroller 820 responds by adjusting the various pacing parameters (such as rate, AV Delay, V-V Delay, etc.) at which the atrial and ventricular pulse generators 822 and 824 generate stimulation pulses.

While shown as being included within the device 700, it is to be understood that a physiologic sensor 870 may also be external to the device 700, yet still be implanted within or carried by the patient. Examples of physiologic sensors that may be implemented in conjunction with device 700 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors 870 may optionally include sensors to help detect movement (via, e.g., a position sensor) and/or minute ventilation (via an MV sensor) in the patient. Signals generated by the position sensor and MV sensor may be passed to the microcontroller 820 for analysis in determining whether to adjust the pacing rate, etc. The microcontroller 820 may thus monitor the signals for indications of the patient's position and activity status, such as whether the patient is climbing up stairs or descending down stairs or whether the patient is sitting up after lying down.

The device 700 additionally includes a battery 876 that provides operating power to all of the circuits shown in FIG. 8. For a device 700 which employs shocking therapy, the battery 876 is capable of operating at low current drains (e.g., preferably less than 10 μA) for long periods of time, and is capable of providing high-current pulses (for capacitor charging) when the patient requires a shock pulse (e.g., preferably, in excess of 2 A, at voltages above 200 V, for periods of 10 seconds or more). The battery 876 also desirably has a predictable discharge characteristic so that elective replacement time can be detected. Accordingly, the device 700 preferably employs lithium or other suitable battery technology.

The device 700 can further include magnet detection circuitry (not shown), coupled to the microcontroller 820, to detect when a magnet is placed over the device 700. A magnet may be used by a clinician to perform various test functions of the device 700 and/or to signal the microcontroller 820 that the external device 854 is in place to receive data from or transmit data to the microcontroller 820 through the telemetry circuit 864.

The device 700 further includes an impedance measuring circuit 878 that is enabled by the microcontroller 820 via a control signal 880. The known uses for an impedance measuring circuit 878 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 700 has been implanted; measuring stroke volume; and detecting the opening of heart valves, etc. The impedance measuring circuit 878 is advantageously coupled to the switch 826 so that any desired electrode may be used.

In the case where the device 700 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 820 further controls a shocking circuit 882 by way of a control signal 884. The shocking circuit 882 generates shocking pulses of low (e.g., up to 0.5 J), moderate (e.g., 0.5 J to 10 J), or high energy (e.g., 11 J to 40 J), as controlled by the microcontroller 820. Such shocking pulses are applied to the patient's heart H through, for example, two shocking electrodes and as shown in this embodiment, selected from a left atrial coil electrode, an RV coil electrode 708, and/or an SVC coil electrode. As noted above, the housing 800 may act as an active electrode in combination with the RV coil electrode 708, and/or as part of a split electrical vector using the SVC coil electrode or the left atrial coil electrode (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 820 is capable of controlling the synchronous or asynchronous delivery of the shocking pulses.

The device 700 also includes or operates in conjunction with components that may provide functionality relating to generating and processing a cardiogenic impedance signal as taught herein. In particular, the device 700 may sense and process thoracic impedance signals and respiratory signals.

Here, sensor signals from an internal sensor (e.g., a sensor 870) and/or an external sensor may be coupled to the microcontroller 820 to obtain a respiratory signal. For example, in some embodiments the switch 826 or some other mechanism may couple signals from the sensor 870 and/or an external sensor connected to terminal 821 to analog circuit components providing the functionality of one or more of the components of FIG. 3. The resulting signals may then be digitized and provided to the microcontroller 820. In some embodiments the signals from the sensor(s) may be coupled to the data acquisition system 852. In this case, the resulting signal data may then be provided to the microcontroller 820 for processing.

The impedance measuring circuit 878 may be adapted to operate in conjunction with the microcontroller 820, a pulse generator (e.g., pulse generator 824) and the switch 826 to obtain a thoracic impedance signal. As discussed above, a series of current pulses may be applied between two or more electrodes to measure transthoracic impedance. In the example of FIG. 8, the microcontroller 820 may initiate the generation of the appropriate pulses by a pulse generator and configure the switch 826 to couple the pulse to the desired electrode(s). In addition, the microcontroller 820 may configure the switch 826 to couple appropriate sense electrodes to the impedance measuring circuit 878. In this way, the impedance measuring circuit 878 may sense voltage signals corresponding to the current pulses to generate a thoracic impedance signal. This signal may then be provided to the microcontroller 820 for further processing. For example, in some embodiments the impedance signal may initially be provided to analog circuit components providing the functionality of one or more of the components of FIG. 3, then digitized and provided to the microcontroller 820. In some embodiments the circuit 878 may generate an impedance signal as digital signal data or the impedance signal may be converted to (e.g., using the data acquisition system 852) digital signal data. In this case, the microcontroller 820 may provide the functionality of the components of FIG. 3.

The microcontroller 820 may thus be adapted to implement several functional components relating to generating and processing a cardiogenic impedance signal as taught herein. Here, the microcontroller may comprise a signal processor or incorporate signal processing or other suitable functionality.

A sensed signal processing component 238 processes a sensed thoracic impedance signal and/or a sensed respiratory signal. For example, the component 238 may filter then store the sensed respiratory signal data and/or the sensed impedance signal data discussed above.

A respiratory signal cancellation component 839 reduces (e.g., cancels) a respiratory component of the sensed impedance signal data. For example, the component 839 may implement the filtering, error detection delaying and combining functionality discussed above.

A cardiogenic impedance derivation component 840 may derive a cardiogenic impedance signal from thoracic impedance signal data after the respiratory component of the thoracic impedance signal has been reduced. Accordingly, the functionality of component 840 may correspond to the functionality discussed above in conjunction with component 320.

A stroke volume calculator component 837 may process cardiogenic impedance signal data to derive stroke volume information. This functionality may include, for example, a portion of the functionality discussed above in conjunction with block 324.

The microcontroller 820 also may implement functionality to analyze the stroke volume information. This functionality may include, for example, a portion of the functionality discussed above in conjunction with block 324. In addition, the device 700 may include a warning/therapy module 834 adapted to generate warning signals and/or administer therapy based on analysis of the cardiac condition of the patient.

Various modifications may be incorporated into the disclosed embodiments based on the teachings herein. For example, the functionality taught herein may be incorporated into different types of devices or combinations of devices other than those types specifically described herein. In addition, the various signals described herein and/or other signals may be sensed in other ways and using different sensing components. Such sensors (e.g., electrodes, physiologic sensors, etc.) also may be incorporated into other types of implantable leads or may be implanted or otherwise provided without the use of leads. These sensors may be located at various positions throughout the heart or the body. Various algorithms and/or techniques may be employed to obtain a cardiac-related signal (e.g. an impedance signal) or a respiratory signal.

It should be appreciated from the above that the various structures and functions described herein may be incorporated into a variety of apparatuses (e.g., a stimulation device, a monitoring device, a lead, etc.) and implemented in a variety of ways. Different embodiments of the stimulation device may include a variety of hardware and software processing components. In some embodiments, hardware components such as processors, controllers, state machines and/or logic may be used to implement the described components or circuits.

In some embodiments, code including instructions (e.g., software, firmware, middleware, etc.) may be executed on one or more processing devices to implement one or more of the described functions or components. The code and associated components (e.g., data structures and other components by the code or to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may simply send raw signal data or processed data to an external device that then performs any necessary processing on the data.

The components and functions described herein may be connected and/or coupled in many different ways. The manner in which this is done may depend, in part, on whether and how the components are separated from the other components. In some embodiments some of the connections and/or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

While certain exemplary embodiments have been described above in detail and shown in the accompanying drawings, it is to be understood that such embodiments are merely illustrative of and not restrictive of the broad invention. In particular, it should be recognized that the teachings herein apply to a wide variety of apparatuses and methods. It will thus be recognized that various modifications may be made to the illustrated and other embodiments described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A cardiac device adapted for implant in a patient, comprising:
    a first sense circuit adapted to obtain a composite signal comprising a cardiac component and a respiratory component;
    a second sense circuit adapted to obtain a respiratory signal; and
    a respiratory signal canceller comprising an adder adapted to subtract the respiratory signal from the composite signal to reduce the respiratory component of the composite signal, and an adaptive filter adapted to adaptively filter the respiratory signal before the respiratory signal is subtracted from the composite signal so that the respiratory signal more closely approximates the respiratory component of the composite signal;
    wherein the adaptive filter is adapted based on at least one prior composite signal that has had a respiratory component reduced through the use of at least one prior respiratory signal obtained via the second sense circuit.

2. A method of deriving a cardiac signal, comprising:
    obtaining an impedance signal comprising a cardiac component, a respiratory component, and a patient motion component;
    obtaining a respiratory signal comprising a patient motion component;
    using the respiratory signal, via a signal canceller, to reduce the respiratory component of the impedance signal and the patient motion component of the impedance signal, wherein reducing the respiratory component of the impedance signal further comprises subtracting the respiratory signal from the impedance signal; and
    adaptively filtering the respiratory signal before subtracting the respiratory signal from the impedance signal so that the respiratory signal more closely approximates the respiratory component of the impedance signal, wherein the adaptive filtering is based on at least one prior impedance signal that has had a respiratory component reduced through the use of at least one prior respiratory signal.

3. A method of deriving a cardiac signal, comprising:
    sensing via a first sense circuit to obtain an impedance signal comprising a cardiac component and a respiratory component;
    sensing via a second sense circuit to obtain a respiratory signal; and
    combining, via a combiner, the respiratory signal with the impedance signal to reduce the respiratory component of the impedance signal;
    wherein the sensing via the second sense circuit comprises sensing at least one of the group consisting of: oxygen saturation, acceleration, blood pressure, and phrenic neural activity, to obtain the respiratory signal.

4. The method of claim 3, further comprising generating a cardiogenic impedance signal from the impedance signal after reduction of the respiratory component.

5. The method of claim 3, further comprising measuring impedance across at least a portion of a thoracic cavity of a patient to obtain the impedance signal.

6. The method of claim 3, wherein the first sense circuit and the second sense circuit are implanted in a patient.

7. The method of claim 3, further comprising processing a signal resulting from the sensing via the second sense circuit to obtain the respiratory signal.

8. The method of claim 3, wherein combining the respiratory signal with the impedance signal further comprises subtracting the respiratory signal from the impedance signal.

9. The method of claim 8, further comprising adaptively filtering the respiratory signal before subtracting the respiratory signal from the impedance signal so that the respiratory signal more closely approximates the respiratory component of the impedance signal.

10. A cardiac device adapted for implant in a patient, said device comprising:
    a first sense circuit adapted to obtain an impedance signal comprising a cardiac component, a respiratory component, and a patient motion component;
    a second sense circuit adapted to obtain a respiratory signal comprising a patient motion component;
    a respiratory signal canceller adapted to use the respiratory signal to reduce the respiratory component of the impedance signal and the patient motion component of the impedance signal, wherein reducing the respiratory component of the impedance signal further comprises subtracting the respiratory signal from the impedance signal; and
    an adaptive filter adapted to adaptively filter the respiratory signal before subtracting the respiratory signal from the impedance signal so that the respiratory signal more closely approximates the respiratory component of the impedance signal, wherein the adaptive filter is further adapted to adapt the filtering based on at least one prior impedance signal that has had a respiratory component reduced through the use of at least one prior respiratory signal.

11. A method of deriving a cardiac signal, comprising:
    obtaining an impedance signal comprising a cardiac component and a respiratory component;
    obtaining a respiratory signal, wherein the obtaining comprises sensing at least one of the group consisting of: oxygen saturation, acceleration, blood pressure, and phrenic neural activity; and
    using the respiratory signal, via a signal canceller, to reduce the respiratory component of the impedance signal.

12. A cardiac device adapted for implant in a patient, comprising:
    a first sense circuit adapted to obtain an impedance signal comprising a cardiac component and a respiratory component;
    a second sense circuit adapted to obtain a respiratory signal; and
    a respiratory signal canceller adapted to combine the respiratory signal with the impedance signal to reduce the respiratory component of the impedance signal;
    wherein the second sense circuit is further adapted to sense a least one of the group consisting of: oxygen saturation, acceleration, blood pressure, and phrenic neural activity, to obtain the respiratory signal.

13. The device of claim 12, wherein:
    the respiratory signal canceller comprises a signal processor; and
    the signal processor is adapted to generate a cardiogenic impedance signal from the impedance signal after reduction of the respiratory component.

14. The device of claim 12, wherein the first sensing circuit is coupled to an implantable lead comprising at least one electrode adapted to sense a signal in the patient to obtain the impedance signal.

15. The device of claim 12, wherein the second sensing circuit is coupled to at least one implantable sensor adapted to sense a signal in the patient to obtain the respiratory signal.

* * * * *